US011524035B2

(12) United States Patent
Otagiri et al.

(10) Patent No.: US 11,524,035 B2
(45) Date of Patent: Dec. 13, 2022

(54) TRANSPLANTATION MEDIUM

(71) Applicants: HEALIOS K.K., Tokyo (JP); SUMITOMO PHARMA CO., LTD., Osaka (JP)

(72) Inventors: Dai Otagiri, Kobe (JP); Tadao Maeda, Kobe (JP)

(73) Assignees: HEALIOS K.K., Tokyo (JP); SUMITOMO PHARMA CO., LTD., Osaka (JP)

( * ) Notice: Subject to any disclaimer, the term of this patent is extended or adjusted under 35 U.S.C. 154(b) by 100 days.

(21) Appl. No.: 16/313,694

(22) PCT Filed: Jun. 29, 2017

(86) PCT No.: PCT/JP2017/023878
§ 371 (c)(1),
(2) Date: Dec. 27, 2018

(87) PCT Pub. No.: WO2018/003908
PCT Pub. Date: Jan. 4, 2018

(65) Prior Publication Data
US 2020/0009196 A1    Jan. 9, 2020

(30) Foreign Application Priority Data

Jun. 30, 2016 (JP) .............................. JP2016-131171

(51) Int. Cl.
| | | |
|---|---|---|
| A61K 35/30 | (2015.01) | |
| A01N 1/02 | (2006.01) | |
| A61K 9/10 | (2006.01) | |
| A61K 47/02 | (2006.01) | |
| A61K 47/34 | (2017.01) | |
| A61L 27/38 | (2006.01) | |
| A61K 47/10 | (2017.01) | |
| A61K 47/20 | (2006.01) | |
| A61K 47/42 | (2017.01) | |
| A61L 27/36 | (2006.01) | |
| A61L 27/50 | (2006.01) | |

(52) U.S. Cl.
CPC ............ *A61K 35/30* (2013.01); *A01N 1/0221* (2013.01); *A61K 9/10* (2013.01); *A61K 47/02* (2013.01); *A61K 47/10* (2013.01); *A61K 47/20* (2013.01); *A61K 47/34* (2013.01); *A61K 47/42* (2013.01); *A61L 27/3687* (2013.01); *A61L 27/3691* (2013.01); *A61L 27/3804* (2013.01); *A61L 27/505* (2013.01); *A61L 2430/16* (2013.01)

(58) Field of Classification Search
None
See application file for complete search history.

(56) References Cited

U.S. PATENT DOCUMENTS

| | | |
|---|---|---|
| 2010/0104542 A1 | 4/2010 | Austen, Jr. |
| 2011/0274662 A1 | 11/2011 | Malcuit et al. |
| 2012/0128641 A1 | 5/2012 | Austen, Jr. |
| 2015/0086512 A1 | 3/2015 | Malcuit et al. |
| 2015/0299653 A1 | 10/2015 | Hovatta et al. |
| 2019/0030168 A1* | 1/2019 | Gay ....................... A61K 47/12 |

FOREIGN PATENT DOCUMENTS

| | | |
|---|---|---|
| JP | 2011-500024 A | 1/2011 |
| JP | 2012-506430 A | 3/2012 |
| JP | 2012-533620 A | 12/2012 |
| JP | 5795961 B2 | 10/2015 |

OTHER PUBLICATIONS

Palomares et al. "Evidence of Pluronic F-68 direct interaction with insect cells: impacton shear protection, recombinant protein, and baculovirus production☆." Enzyme and microbial technology 26.5-6 (2000): 324-331. (Year: 2000).*
Gabrielian et al. "Cellular response in rabbit eyes after human fetal RPE cell transplantation." Graefe's Archive for Clinical and Experimental Ophthalmology 237.4 (1999): 326-335. (Year: 1999).*
STEMCELL Technologies "TeSR™2: Defined, Feeder-Free and Eno-Free Human ES and iPS Cell Medium" available from company webpage, accessed Jul. 8, 2021 (https://www.stemcell.com/media/files/brochure/BRDX20261-TeSR2_Defined_Feeder_Free_Xeno_Free_Human_ESJPS_Cell_Medium.pdf), copyright 2016 (Year: 2016).*
Stalmans et al. "Confocal imaging of Ca2+ signaling in cultured rat retinal pigment epithelial cells during mechanical and pharmacologic stimulation." Investigative Ophthalmology & Visual Science 38.1 (1997): 176-187. (Year: 1997).*
Moloughney et al., "Poloxamer 188 (P188) as a Membrane Resealing Reagent in Biomedical Applications," *Recent Pat. Biotechnol.*, 6(3): 200-211 (2012).
Palomares et al., "Evidence of Pluronic F-68 direct interaction with insect cells: impact on shear protection, recombinant protein, and baculovirus production," *Enzyme Microb. Technol.*, 26(5-6): 324-331 (2000).
Schwartz et al., "Embryonic stem cell trials for macular degeneration: a preliminary report," *Lancet*, 379(9817): 713-720 (2012).
Serbest et al., "Mechanisms of cell death and neuroprotection by poloxamer 188 after mechanical trauma," *FASEB J.*, 20(2): 308-310 (2006) [e-publication 10.1096/fj.05-4024fje (Dec. 31, 2005)].

(Continued)

*Primary Examiner* — Emily A Cordas
(74) *Attorney, Agent, or Firm* — Leydig, Voit & Mayer, Ltd.

(57) ABSTRACT

The present invention, in which RPE cells are suspended in a medium pharmaceutically acceptable as an ocular irrigating/washing solution and containing a poloxamer, achieves improvement of the post-thawing survival rate of cryopreserved RPE cells, improvement of the photoreceptor cell protection effect by RPE cell transplanted immediately after thawing, and prevention of loss of RPE cells in various steps from thawing to transplantation.

11 Claims, 6 Drawing Sheets

(56) References Cited

OTHER PUBLICATIONS

Japanese Patent Office, International Search Report in International Patent Application No. PCT/JP2017/023878 (dated Aug. 15, 2017).
Steinhardt et al., "Poloxamer 188 Enhances Endothelial Cell Survival in Bovine Corneas in Cold Storage," *Cornea*, 25(7): 839-844 (2006).
European Patent Office, Extended European Search Report in European Patent Application No. 17820262.8 (dated Nov. 19, 2019).
Saito et al., "Pluronic Surfactants," *Journal of Japan Oil Chemists' Society*, 49(10): 1071-1080 (2000).
Japanese Patent Office, Notice of Reasons for Refusal in Japanese Patent Application No. 2018-525252 (dated Sep. 28, 2021).
Korean Intellectual Property Office, Decision for Grant of Patent in Korean Patent Application No. 10-2019-7002915 (dated Jul. 10, 2022).

\* cited by examiner

A.

B.

TRANSPLANTATION MEDIUM

CROSS-REFERENCE TO RELATED APPLICATIONS

This patent application is the U.S. national phase of International Patent Application No. PCT/JP2017/023878, filed Jun. 29, 2017, which claims the benefit of Japanese Patent Application No. 2016-131171, filed on Jun. 30, 2016, which are incorporated by reference in their entireties herein.

TECHNICAL FIELD

The present invention relates to a suspending agent for retinal pigment epithelial (RPE) cells, an RPE cell-containing composition suspended in the suspending agent, and a production method of an RPE cell-containing composition, comprising suspending RPE cells in the suspending agent, and the like.

BACKGROUND ART

Retinal pigment epithelial (RPE) cells exist in the outermost layer of the retina as one layer of epithelial cell tissue accompanied by pigment, and play an extremely important role in maintaining the function of the eye ball retina which is responsible for vision. Representative functions thereof include neogenesis of outer segment of retinal photoreceptor cell due to phagocytotic function, recycling of visual substances that are photosensitive proteins specifically present in the outer segment of photoreceptor cell, protection effect on photoreceptor cells and choroid membrane, which are neighboring tissues of RPE, by secretion of various cytokines, and the like. It is known, therefore, that when RPE cells become dysfunctional due to aging, genetic abnormality and the like, resulting in degeneration and cell death associated therewith, serious retinal denaturation such as macular degeneration such as age-related macular degeneration (AMD), Stargardt disease and the like or retinitis pigmentosa (RP) and the like is developed. In particular, AMD is an ophthalmic disease that causes impairment of central vision and sight loss in elderly people, and poses an important social problem in developed countries including Japan, which will become unprecedented aging societies hereafter. Presently, the treatment method for AMD is generally an intraocular administration of antibody medicine, which is a symptomatic treatment, and an effective treatment method has still not been established. Thus, the development of an alternative curative treatment method is desired. Furthermore, an effective treatment method for Stargardt disease and RP has not been established at all to date.

In recent years, a cell transplantation therapy including supplementing or substituting RPE cells induced to differentiate from pluripotent stem cells is attracting attention as a new treatment method of AMD and RP. Thus, utilization of RPE cells as a graft material for cell therapy is expected. For example, Ocata Therapeutics, Inc. (formerly Advanced Cell Technology (ACT), Inc.) is undertaking clinical research on age-related macular degeneration (AMD) and Stargardt disease using RPE cells derived from human embryonic stem cells (ES cells) (non-patent document 1). In Japan, surgery to transplant an RPE cell sheet derived from human induced pluripotent stem cells (iPS cells) to exudative AMD patient was conducted in 2014. The surgery attracted much attention as the world's first iPS cell transplantation therapy, and it is reported that the treatment progress is still good now.

Currently, transplantation of RPE cells includes (1) a method of transplanting a prepared RPE cell sheet or an RPE cell sheet with scaffold, which is prepared by seeding RPE cells on a scaffold material, to a part where the retinal pigment epithelium is denatured or defective from an incision formed in the retina, or (2) a method of injecting an RPE cell suspension into a similar part. Cultivation of cells for transplantation needs to be performed at a GMP level. In the former case, therefore, the RPE cell sheet after production is transported from a cell processing center (CPC) to a facility (hospital) where transplant operation is performed. On the other hand, in the latter case, in a clinical trial conducted by Ocata Therapeutics, for example, cryopreserved RPE cells produced in CPC are transported to a hospital and, in the hospital, the cells are thawed, suspended in a transplantation medium, immediately brought into an operating room, and transplanted. The latter is considered highly convenient since the cells can be transported from CPC to the hospital in a frozen state.

Nevertheless, the possibility that the freeze-thaw treatment causes damage on the graft cells cannot be denied. Conventionally, terminally differentiated cells and tissues used for topical transplantation were generally provided by transplantation between living bodies or production free of freezing step. When cryopreserved cells were transplanted unavoidably, the freeze-thaw step was feared to cause damage on the structure of the cells and tissues and deterioration of functions thereof. Suppression of decline in the function of cryopreserved cells is a big task in realizing localized cell transplantation therapy. An influence of transplantation of RPE cells immediately after thawing on the therapeutic effect has not been studied so far.

Poloxamer 188 (polyoxyethylene(160)polyoxypropylene(30)glycol) is known to exhibit cell protection effects by repairing physically or chemically damaged cell membranes. Several patents and patent applications have heretofore been made relating to the use of poloxamer 188 as a cell membrane sealing agent in the treatment of pathological conditions such as muscular dystrophy, heart failure, neurodegenerative diseases, electrical damage and the like and medical applications such as transplantation and the like (non-patent document 2). For example, Austen et al. discloses a method of sealing cell membrane of adipose tissues damaged during liposuction with poloxamer 188 (patent document 1). They further disclose a method of improving the survival rate of cryopreserved cells by thawing the cryopreserved cells in the presence of poloxamer 188 (patent document 2).

However, there has been no report to date on the use of poloxamer 188 during implantation of RPE cells or thawing of cryopreserved RPE cells.

DOCUMENT LIST

Patent Documents patent document 1: JP-B-5795961
patent document 2: National Publication of International Patent Application No. 2012-533620

Non-Patent Documents non-patent document 1: Schwartz et al., Lancet, 379: 713-720 (2012)
non-patent document 2: Moloughney et al., Recent Pat. Biotechnol., 6(3): 200-211 (2012)

SUMMARY OF THE INVENTION

Problems to be Solved by the Invention

An object of the present invention is to provide an RPE cell suspending agent suitable for use for RPE cells for the treatment of retinal degenerative diseases such as macular degeneration, retinitis pigmentosa (RP) and the like, a composition containing RPE cells suspended in the suspending agent, a method for producing an RPE cell-containing composition suitable for transplantation, including suspending RPE cells in the suspending agent, and the like.

Means of Solving the Problems

The present inventors have conducted intensive studies in an attempt to achieve the aforementioned objects and found that the post-thawing survival rate and the post-thawing recovery rate of cryopreserved RPE cells are improved by adding poloxamer 188 to a transplantation medium (suspending agent) to be added after thawing.

In clinical trials on macular degeneration by using ES cell-derived RPE cells, cryopreserved RPE cells were transplanted immediately after thawing (the above-mentioned non-patent document 1). From the above-mentioned results, the present inventors have had an idea that transplantation of RPE cells immediately after thawing may decrease the cell viability and deteriorate the cell condition, which in turn may impair the transplantation effects (e.g., photoreceptor cell protection effect). The photoreceptor cell protection effect was compared between transplantation of RPE cells immediately after thawing and that after culturing for a certain period after thawing to RCS (Royal College of Surgeons) rats, which are retinal degeneration models. As a result, it was clarified that the latter showed a higher photoreceptor cell protection effect.

The present inventors have conducted intensive studies in an attempt to prevent reduction of a photoreceptor cell protection effect in the RPE cells immediately after thawing. As a result, RPE cells showed, even immediately after thawing, a high photoreceptor cell protection effect equivalent or superior to that after incubation for a certain period, when poloxamer 188 was added to the transplantation medium. The results show that, by the use of poloxamer, a high transplantation effect can be obtained even when RPE cells in a cryopreserved state are transported into a hospital and transplanted immediately after thawing, without once culturing the RPE cells in CPC after thawing from cryopreservation.

Furthermore, the present inventors have tested whether the addition of poloxamer 188 to the transplantation medium can contribute to not only the survival rate and transplantation effect of RPE cells after thawing but also reduction of the loss of RPE cells during various operations from thawing to transplantation (improvement of cell recovery rate). As a result, it was clarified that all of the loss of cells after thawing, loss of cells by a centrifugation operation, and loss of cells when passing a transplantation device can be reduced by using a poloxamer 188-containing medium as a suspending agent from the steps of dilution and washing operation immediately after thawing.

Based on these findings, the present inventors have found m that use of a suspending agent containing poloxamer 188 as a medium for transplantation is useful for simplification and speeding up of transplantation protocol, improvement and equalizing of transplantation effect, and further, cost reduction in the RPE cell transplantation treatment, which resulted in the completion of the present invention.

That is, the present invention provides the following.

[1] A suspending agent for retinal pigment epithelial (RPE) cells, comprising a poloxamer and a medium pharmaceutically acceptable as an ocular irrigating/washing solution.

[2] The suspending agent of [1], wherein the medium is a modified Hank's Balanced Salt Solution or an oxyglutathione-containing ocular irrigating/washing solution.

[3] The suspending agent of [1] or [2], wherein a concentration of the poloxamer is 0.001% (w/v)-0.1% (w/v).

[4] The suspending agent of [1] or [2], wherein a concentration of the poloxamer is 0.01% (w/v)-0.1% (w/v).

[5] The suspending agent of any of [1] to [4], for transplanting cryopreserved RPE cells without culturing the cells.

[6] The suspending agent of any of [1] to [5], for transplanting within 8 hr after thawing.

[7] The suspending agent of any of [1] to [6], as a protector of RPE cells.

[8] The suspending agent of any of [1] to [7], which is used in any step after thawing and up to transplantation and suppresses a decrease in the number of RPE cells before and after the step.

[9] A pharmaceutical composition for transplantation, comprising an RPE cell and a poloxamer.

[10] The pharmaceutical composition of [9], wherein the RPE cell is suspended in a poloxamer-containing medium pharmaceutically acceptable as an ocular irrigating/washing solution.

[11] The pharmaceutical composition of [10], wherein the medium is a modified Hank's Balanced Salt Solution or an oxyglutathione-containing ocular irrigating/washing solution.

[12] The pharmaceutical composition of [10] or [11], wherein a concentration of the poloxamer in the medium is 0.001% (w/v)-0.1% (w/v).

[13] The pharmaceutical composition of [10] or [11], wherein a concentration of the poloxamer in the medium is 0.01% (w/v)-0.1% (w/v).

[14] The pharmaceutical composition of any of [9] to [13], wherein the RPE cell is a cell within 1 hr after thawing from cryopreservation, and wherein the pharmaceutical composition is transplanted to a subject within 8 hr after preparation.

[15] The pharmaceutical composition of any of [9] to [14], showing an improved survival rate of RPE cells compared to that without containing a poloxamer.

[16] The pharmaceutical composition of any of [9] to [15], showing an improved recovery rate of RPE cells compared to that without containing a poloxamer.

[17] A method for producing an RPE cell-containing composition, comprising suspending an RPE cell in a poloxamer-containing medium pharmaceutically acceptable as an ocular irrigating/washing solution.

[18] The method of [17], wherein the medium is a modified Hank's Balanced Salt Solution or an oxyglutathione-containing ocular irrigating/washing solution.

[19] The method of [17] or [18], wherein a concentration of the poloxamer in the medium is 0.001% (w/v)-0.1% (w/v).

[20] The method of [17] or [18], wherein a concentration of the poloxamer in the medium is 0.01% (w/v)-0.1% (w/v).

[21] The method of any of [17] to [20], wherein the RPE cell is a cell within 1 hr after thawing from cryopreservation and the RPE cell-containing composition is a pharmaceutical composition for transplantation to be transplanted to a subject within 8 hr after preparation.

[22] The method of any of [17] to [21], showing an improved survival rate of RPE cells compared to that without containing a poloxamer.

[23] The method of any of [17] to [22], showing an improved recovery rate of RPE cells compared to that without containing a poloxamer.

[24] The pharmaceutical composition of any of [9] to [16], for protection of a photoreceptor cell.

[25] The suspending agent of any of [1] to [8], wherein the poloxamer is poloxamer 188. [26] The pharmaceutical composition of any of [9] to [16] and [24], wherein the poloxamer is poloxamer 188.

[27] The method of any of [17] to [23], wherein the poloxamer is poloxamer 188.

Effect of the Invention

According to the present invention, the post-thawing survival rate and the post-thawing recovery rate of cryopreserved RPE cells can be improved using a poloxamer. The effect lasts for a long time even at an ordinary temperature and enables preservation and transportation at an ordinary temperature after preparation of a cell suspension for transplantation.

Using a poloxamer, RPE cells cryopreserved and transplanted immediately after thawing show a photoreceptor cell protection effect equal to or higher than that of RPE cells transplanted after culturing for a given period after thawing. Thus, RPE cells in a frozen state can be transported from CPC to a hospital and transplanted immediately after thawing in the hospital. This enables simplification of transplantation protocol and shortening of the time before performing transplantation.

Furthermore, using a poloxamer, loss of RPE cells in each step from thawing to transplantation can be reduced and the number of cells can be equalized. Thus, the number of RPE cells to be prepared for ensuring a sufficient number of cells for transplantation can be reduced. In addition, variability of the survival rate and the number of transplanted cells can be decreased in every transplantation. Thus, the treatment effect can be equalized and safety in terms of prevention of administration of damaged cells can be improved.

DESCRIPTION OF EMBODIMENTS

Figure 1:
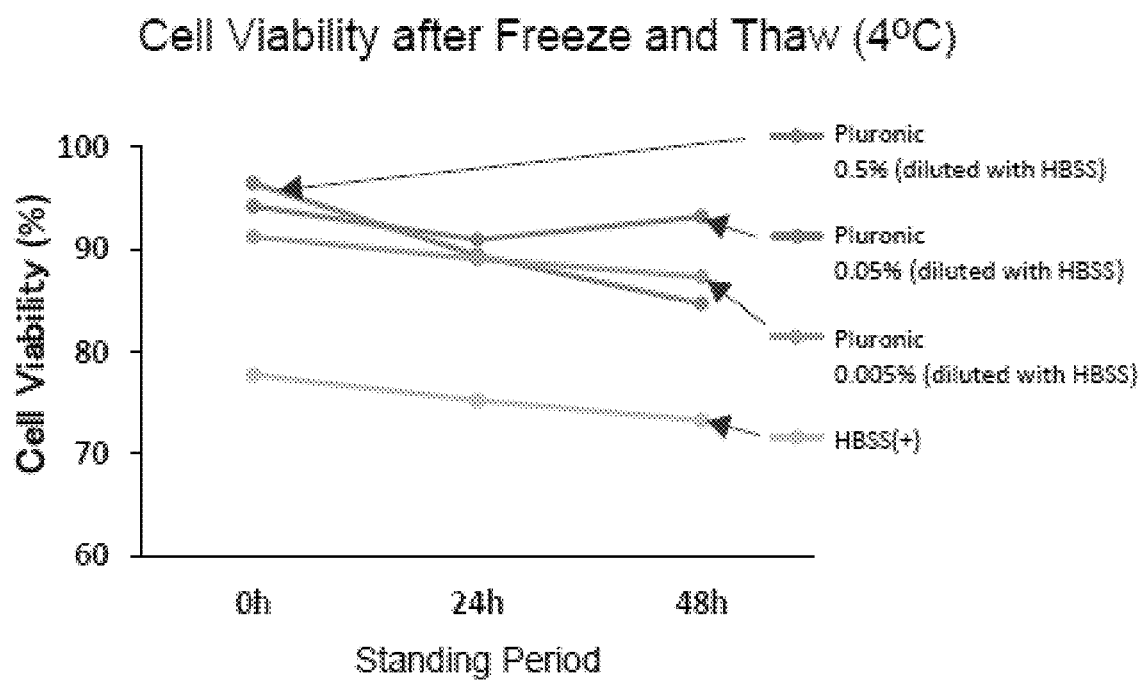
FIG. 1 shows the effect of various concentrations of poloxamer 188 on the survival rate of RPE cells stood at 4° C. for 48 hr after freeze-thawing.
Figure 1:
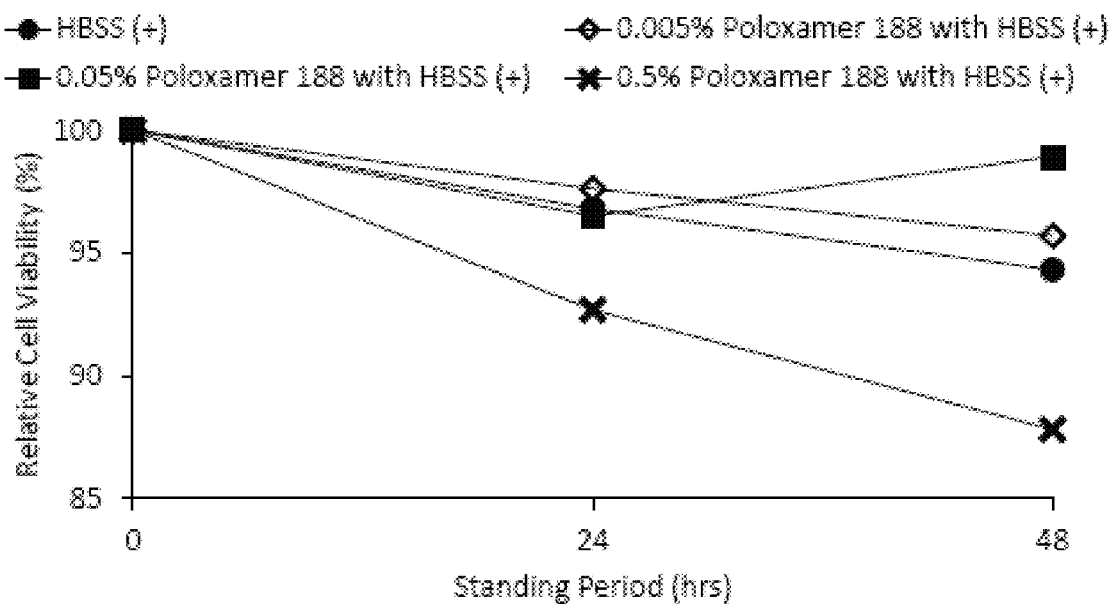

The present invention provides a suspending agent for retinal pigment epithelial (RPE) cells, comprising a poloxamer and a medium pharmaceutically acceptable as an ocular irrigating/washing solution. The present invention also provides a pharmaceutical composition for transplantation, comprising RPE cells and a poloxamer.

(A) Retinal Pigment Epithelial (RPE) Cell

In the present specification, "retinal pigment epithelial (RPE) cell" refers to an epithelial cell constituting the retinal pigment epithelium, and a progenitor cell thereof. Whether a cell is a retinal pigment epithelial cell can be confirmed by, for example, expression of cell marker (RPE65, CRALBP, MERTK, BEST1 etc.), cell morphology (intracellular melanin pigment deposition, polygonal, flat epithelium-like cell morphology, polygonal actin bundle formation, etc.) and the like. Progenitor cell of retinal pigment epithelial cell means a cell in which induction of differentiation into retinal cell is programmed. Whether a cell is the progenitor cell can be confirmed by expression of cell marker (Mitf (pigment epithelial cell, pigment epithelial progenitor cell), Pax6 (pigment epithelial progenitor cell), Rx (retinal progenitor cell), OTX2 (retinal progenitor cell), RPE65 (pigment epithelial cell), BEST1 (pigment epithelial cell)) and the like. Functional evaluation of retinal pigment epithelial cell can be confirmed, for example, using the secretory activity of cytokines (VEGF, PEDF, etc.), phagocytotic activity and the like as indexes. Those skilled in the art can perform such functional evaluation and confirmation operation by setting conditions as appropriate.

RPE cell can be obtained from any animal having RPE cells or can also be obtained from pluripotent stem cell, etc. by inducing differentiation according to a method known per se. Examples of the RPE cell include one obtained by, for example, inducing differentiation from pluripotent stem cell. The pluripotent stem cell is not particularly limited as long as it has pluripotency permitting differentiation into any cell present in living organisms, and also has proliferative capacity. For example, embryonic stem cell (ES cell), clone embryo-derived embryonic stem cell (ntES cell) obtained by nuclear transplantation, germline stem cell (GS cell), m embryonic germ cell (EG cell), induced pluripotent stem cell (iPS cell), pluripotent cell derived from cultured fibroblast or myelogenic stem cell (Muse cell), and the like are included. Preferable pluripotent stem cells are ES cell and iPS cell. The derivation of the pluripotent stem cell is not particularly limited and, for example, any animal, preferably mammal, more preferably human, mouse, rat and the like, in which establishment of any of the following pluripotent stem cells has been reported, can be mentioned.

ES cell is an embryo-derived stem cell derived from an inner cell mass of a blastocyst, which is an embryo after morula in 8-cell phase of a fertilized egg, and has the ability to differentiate into various cells constituting an adult, what is called pluripotency, and proliferation potency by self-renewal. ES cell was found in mouse in 1981 (M. J. Evans and M. H. Kaufman (1981), Nature 292:154-156), after which ES cell line was also established in primates such as human, monkey and the like (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cell can be established by removing an inner cell mass from a blastocyst of a fertilized egg of a subject animal and culturing the inner cell mass on a fibroblast feeder. In addition, the cells can be maintained by passage culture using a culture medium added with a substance such as leukemia inhibitory factor (LIF), basic fibroblast growth factor (bFGF) and the like. The methods for establishing and maintaining ES cells of human and monkey are described in, for example, U.S. Pat. No. 5,843,780; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103: 9554-9559; H. Suemori et al. (2001), Dev. Dyn., 222:273-279; H. Kawasaki et al. (2002), Proc. Natl. Acad. Sci. USA, 99:1580-1585; Klimanskaya I, et al. (2006), Nature. 444: 481-485 and the like.

An iPS cell is a somatic cell-derived artificial stem cell having properties almost equivalent to those of ES cells, such as pluripotency and proliferation potency by self-renewal, and can be produced by introducing a particular reprogramming factor in the form of a DNA or protein into a somatic cell (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666).

The term "somatic cell" used in the present specification refers to any animal cell (preferably, cells of mammals inclusive of human) except germ line cells and totipotent cells such as ovum, oocyte, ES cell and the like. The somatic cell nonlimitatively encompasses any of somatic cells of the fetus (pup), somatic cells of the newborn (pup), and matured healthy or diseased somatic cells and encompasses any of primary culture cells, subcultured cells and established lines of cells. To be specific, examples of the somatic cell include (1) tissue stem cell (somatic stem cell) such as neural stem cell, hematopoietic stem cell, mesenchymal stem cell, pulp stem cell and the like, (2) tissue progenitor cell, (3) differentiated cell such as lymphocyte, epithelial cell, endothelial cell, muscle cell, fibroblast (skin cell etc.), hair cell, hepatocyte, gastric mucosa cell, enterocyte, splenocyte, pancreatic cell (pancreatic exocrine cell etc.), brain cell, lung cell, kidney cell, fat cell and the like, and the like.

The reprogramming factor may be composed of a gene that is specifically expressed in ES cells, a gene product or non-coding RNA thereof or a gene that plays an important role in maintaining undifferentiation state of ES cell, a gene product or non-coding RNA thereof, or a low molecular weight compound. Examples of the gene contained in the reprogramming factor include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, Glis1 and the like, and these reprogramming factors may be used alone or in combination. Examples of the combinations of the reprogramming factors include those recited in WO 2007/069666, WO 2008/118820, WO 2009/007852, WO 2009/032194, WO 2009/058413, WO 2009/057831, WO 2009/075119, WO 2009/079007, WO 2009/091659, WO 2009/101084, WO 2009/101407, WO 2009/102983, WO 2009/114949, WO 2009/117439, WO 2009/126250, WO 2009/126251, WO 2009/126655, WO 2009/157593, WO 2010/009015, WO 2010/033906, WO 2010/033920, WO 2010/042800, WO 2010/050626, WO 2010/056831, WO 2010/068955, WO 2010/098419, WO 2010/102267, WO 2010/111409, WO 2010/111422, WO 2010/115050, WO 2010/124290, WO 2010/147395, WO 2010/147612, Huangfu D, et al. (2008), Nat. Biotechnol., 26: 795-797, Shi Y, et al. (2008), Cell Stem Cell, 2: 525-528, Eminli S, et al. (2008), Stem Cells. 26:2467-2474, Huangfu D, et al. (2008), Nat Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci USA. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, Mali P, et al. (2010), Stem Cells. 28:713-720, and Maekawa M, et al. (2011), Nature. 474:225-9.

Examples of the method for inducing differentiation of ES m cell into RPE cell include, but are not limited to, SDIA method (PNAS, 99: 1580-1585, 2002), SFEB method (Nat. Biotechnol., 26: 215-224, 2008) and the like. In addition, differentiation of RPE cell from iPS cell can be induced by a similar method (e.g., Neurosci. Lett., 458: 126-131, 2009; PLoS One, 8: 409-412, 2011). Alternatively, the methods described in WO 2015/053375, WO 2015/053376, WO 2015/125941, WO 2017/043605 and the like can also be used.

As the RPE cell in the present specification, RPE cell induced to differentiate from human ES cell or human iPS cell can be specifically mentioned.

RPE cell to which the suspending agent of the present invention is applied or RPE cell contained in the pharmaceutical composition of the present invention is preferably an RPE cell within 1 hr or 20 min after thawing, or immediately after thawing from a cryopreserved state. The RPE cell prepared as mentioned above is cryopreserved according to a method known per se and thawed immediately before suspending in the suspending agent of the present invention. Examples of the cryopreservation method of RPE cell include, but are not limited to, a method including recovering RPE cells in a centrifugation tube or the like, pelletizing the cells by centrifugation, suspending the cells in a cryopreservation solution containing a cryoprotective agent, placing the suspension in a cryopreservation tube, freezing same by a freezer at −80° C. and preserving same in a gaseous phase or liquid phase in a nitrogen tank, and the like. As the cryoprotective agent, for example, DMSO, glycerol, antifreeze protein, antifreeze glycoprotein and the like can be used as appropriate.

As a method for thawing the cryopreserved RPE cells, a method well known in the pertinent technical field can be used (e.g., Freshney R I, Culture of Animal cells: A Manual of Basic Technique, 4th Edition, 2000, Wiley-Liss, Inc., Chapter 19). Preferably, the cells are rapidly thawed in a hot-water bath at about 37° C. When a highly cytotoxic cryoprotective agent such as DMSO is used, it is desirable to dilute DMSO immediately after thawing with a suitable diluent to a concentration free of an adverse influence on the cell. It is desirable to remove toxic cryoprotective agents and the like by removing the supernatant by centrifugation. As the diluent, serum-containing or serum-free medium, saline or PBS can be used, and a pharmaceutically acceptable medium is also preferably used as the ocular irrigating/washing solution in the suspending agent of the present invention.

(B) Poloxamer

In the present DESCRIPTION, the "poloxamer" is a triblock copolymer represented by the following structural formula:

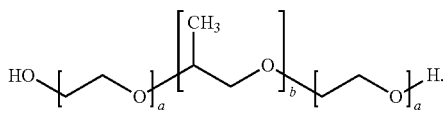

Examples of the poloxamer include poloxamer 124, poloxamer 188, poloxamer 237 and poloxamer 407, and preferred are poloxamer 188 and poloxamer 237, and more preferred is poloxamer 188.

Poloxamer 188 (in the formula, a=80, b=30) is used as a pharmaceutical additive for applications such as stable (stabilizing) agent, surfactant, lubricant, soluble (solubilizing) agent, base, binder, suspension (suspending) agent, coating agent, wetting agent, emulsifier, thickening agent, excipient, dispersing agent, disintegrant, solubilizing agent and the like and can be used safely.

Poloxamer 188 can be produced by a method known per se. Poloxamer 188 is commercially available under the trade names of, for example, Pluronic (registered trade mark) F68 (BASF), Pluronic F68 10% (100×) (Thermo Fisher Scientific (former Life Technologies)), PRONON (registered trade mark) #188P (NOF CORPORATION) and the like.

The concentration of the poloxamer, for example, poloxamer 188, contained in the suspending agent of the present invention, or the medium in the pharmaceutical composition of the present invention is not particularly limited as long as it is sufficient for, for example, protecting RPE cells, particularly, RPE cells thawed from cryopreservation, suppressing cell damage or cell death (RPE cell protection effect), improving photoreceptor cell protection effect (prevention of decrease) of RPE cell, and/or preventing a loss in the number of RPE cells in various steps from thawing to transplantation. It is preferably 0.001% (w/v)-0.1% (w/v), more preferably 0.01% (w/v)-0.1% (w/v) (e.g., 0.01% (w/v)-less than 0.1% (w/v), 0.01% (w/v)-0.09% (w/v), 0.08% (w/v), 0.07% (w/v), 0.06% (w/v) or 0.05% (w/v) etc.). In consideration of the concentration of poloxamer 188 necessary for preventing cell death during "thawing" of cryopreserved adipose tissue, which is 0.1 to 2% (w/v) or not less than that (the above-mentioned patent document 2), it is a surprising finding that a superior RPE cell protection effect is achieved by adding a poloxamer at a low concentration of less than 0.1% (w/v) "after thawing".

(C) Pharmaceutically Acceptable Medium as Ocular Irrigating/Washing Solution

The "medium pharmaceutically acceptable as ocular irrigating/washing solution" contained in the suspending agent of the present invention and the pharmaceutical composition of the present invention is not particularly limited as long as it is a suspension in which RPE cells are suspended in a medium and direct injection thereof into the disease site, namely, degenerative or defective site of the subretinal pigmented epithelium in macular degeneration or retinitis pigmentosa is pharmaceutically acceptable. For example, buffering agent, isotonicity agent, viscosity base, chelating agent, pH adjuster, antioxidant and the like can be appropriately selected and contained at a range free from an influence on the survival rate of the RPE cell.

Examples of the buffering agent include phosphoric acid buffering agent, boric acid buffering agent, citrate buffering agent, tartaric acid buffering agent, acetate buffering agent, amino acid and the like.

Examples of the tonicity agent include saccharides such as sorbitol, glucose, mannitol and the like, polyhydric alcohols such as glycerol, propylene glycol and the like, salts such as sodium chloride and the like, boric acid and the like.

Examples of the viscous base include water-soluble polymers such as polyvinylpyrrolidone, polyethylene glycol, poly(vinyl alcohol) and the like, celluloses such as hydroxyethylcellulose, methylcellulose, hydroxypropylmethylcellulose, sodium carboxymethylcellulose and the like, and the like.

Examples of the chelating agent include sodium edetate, citric acid and the like.

Examples of the pH adjuster include sodium hydroxide, potassium hydroxide, sodium carbonate, sodium hydrogen carbonate, boric acid or a salt thereof (borax), hydrochloric acid, citric acid or a salt thereof (sodium citrate, citric acid dihydrogen sodium etc.), phosphoric acid or a salt thereof (disodium hydrogen phosphate, potassium dihydrogen phosphate etc.), acetic acid or a salt thereof (sodium acetate, ammonium acetate etc.), tartaric acid or a salt thereof (sodium tartrate etc.) and the like.

Examples of the antioxidant include glutathione, sodium hydrogen sulfite, dry sodium sulfite, sodium pyrrosulfite, tocopherol and the like.

The pH of the agent of the present invention is generally adjusted to about 5.0-about 8.5, preferably about 7.0-about 8.0. Preferably, a sterilization treatment such as sterilization by filtration using a membrane filter and the like, and the like can be performed.

In one preferable embodiment of the present invention, as the "medium pharmaceutically acceptable as ocular irrigating/washing solution", modified Hank's Balanced Salt Solution (HBSS) or oxyglutathione-containing ocular irrigating/washing solution can be used. Examples of the modified HBSS include phenol red-free HBSS(−) (400 mg/L KCl, 8 g/L NaCl, 350 mg/L NaHCO$_3$, 60 mg/L KH$_2$PO$_4$, 47.9 mg/L anhydrous Na$_2$HPO$_4$, 1 g/L D-glucose; hereinafter to be also simply referred to as "HBSS(−)"), phenol red-free HBSS(+) (HBSS(−) added with 140 mg/L anhydrous CaCl$_2$, 100 mg/L MgCl$_2$.6H$_2$O, 100 mg/L MgSO$_4$.7H$_2$O; hereinafter to be also simply referred to as "HBSS(+)") and the like. Examples of the modified ocular irrigating/washing solution containing oxyglutathione include BSS plus (registered trade mark) intraocular irrigating solution 0.0184% (Nihon Alcon) (hereinafter to be also simply referred to as "BSS") and the like.

(D) Suspending Agent of the Present Invention•Pharmaceutical Composition of the Present Invention The suspending agent of the present invention can be prepared by adding an appropriate amount of a poloxamer (e.g., poloxamer 188) to the medium pharmaceutically acceptable as ocular irrigating/washing solution of the above-mentioned (C). The pharmaceutical composition of the present invention can be prepared by suspending the above-mentioned RPE cells in the suspending agent of the present invention.

As mentioned above, in one preferable embodiment of the present invention, the RPE cells suspended in the suspending agent of the present invention and prepared as the pharmaceutical composition of the present invention are cells immediately after thawing from a cryopreserved state. The cryopreserved RPE cells immediately after thawing by the above-mentioned method are desirably diluted with a suitable diluent and washed by centrifugation. As the diluent here, as mentioned above, saline, PBS, and the medium (e.g., HBSS(+), BSS etc.) pharmaceutically acceptable as the ocular irrigating/washing solution of the above-mentioned (C) can be used. The diluent may or may not contain a poloxamer (e.g., poloxamer 188). To suppress damage on or cell death of RPE cells in the washing step by centrifugation, and prevent a loss in the number of cells during operations, it is preferable to add poloxamer 188 to the diluent. That is, in one embodiment, the dilution and washing steps are performed in a medium pharmaceutically acceptable as an ocular irrigating/washing solution containing a poloxamer (e.g., poloxamer 188), whereby an RPE cell protection effect, or a suppressive effect on the damage on or cell death of RPE cell is acknowledged, and the recovery rate of the RPE cells is improved. Therefore, a method of protecting RPE cells, a method of suppressing damage on or cell death of RPE cells, and a method of improving the recovery rate of RPE cells, by suspending the RPE cells in a medium pharmaceutically acceptable as an ocular irrigating/washing solution and containing a poloxamer (e.g., poloxamer 188), are also encompassed in the present invention. The addition concentration of the poloxamer is similarly preferably exemplified by the concentration range of the poloxamer in the suspension of the present invention. The dilution and washing steps may be performed from room temperature to about 37° C., or under cooling at about 4° C. The washing operation may be performed only once, or can be repeated two to several times.

By resuspending the diluted and washed RPE cells in the suspending agent of the present invention, the pharmaceutical composition of the present invention, namely, an RPE cell-containing composition, can be obtained. The RPE cell in the pharmaceutical composition of the present invention is an RPE cell within 1 hr, further preferably 20 min, after thawing from a cryopreserved state. The density of the RPE cell in the pharmaceutical composition of the present invention is not particularly limited as long as a therapeutically effective amount of RPE cell is contained in a suspension (e.g., 50-500 µL, preferably 100-300 µL) to be injected into a diseased site, namely, a defective site of retinal pigment epithelium in macular degeneration and retinitis pigmentosa. For example, the RPE cells can be suspended to a cell density of 100-20,000 cells/µL, preferably 1,000-10,000 cells/µL. In a clinical trial using ES cell-derived RPE cells on macular degeneration, live RPE cells were suspended in BSS finally to 333 cells/µL and the cell suspension (150 µL, total number of live RPE cells, 50,000 cells) was injected into a macular area (the above-mentioned non-patent document 1). The pharmaceutical composition of the present invention containing a poloxamer (e.g., poloxamer 188) can protect RPE cells, remarkably suppress damage on and cell death of RPE cells, and remarkably prevent cell loss during a centrifugation step for the dilution and the washing, resuspending thereof, and passage of a transplantation device (syringe etc.) during transplantation thereof more than when RPE cells were suspended in a medium (e.g., BSS) alone. Therefore, the number of starting RPE cells required to make an equal amount of live RPE cells as in the conventional method arrive at the transplant site can be decreased, and the cost and time required for preparation of RPE cells necessary for transplantation can be reduced.

The pharmaceutical composition of the present invention obtained by suspending cryopreserved RPE cells immediately after thawing in the suspending agent of the present invention does not show a decrease in the survival rate of RPE cells even when stood at 4° C. for at least 48 hr or at ordinary temperature for at least 8 hr. This means advantages are present that RPE cells cryopreserved in a CPC can be thawed, prepared as a preparation for transplantation, and transported under cooling or at ordinary temperature to a hospital where transplantation is performed, as a result of which complications in transportation can be eliminated and transplantation can be performed immediately after arrival at the hospital. That is, in one embodiment, cryopreserved RPE cells immediately after thawing are suspended in the suspending agent of the present invention, whereby the RPE cells can be transplanted to a subject patient within 48 hr, preferably 8 hr, after thawing. Therefore, a method for transplanting RPE cell to a patient, including the following steps:

(1) a step of thawing cryopreserved RPE cells,
(2) a step of suspending the thawed RPE cells in the suspension of the present invention, and
(3) a step of administering the suspension containing the RPE cells obtained in (2) to an eye tissue of the patient within 48 hr, preferably within 8 hr, after thawing is also within the scope of the present invention.

On the other hand, even when the pharmaceutical composition of the present invention is used for transplantation immediately after suspending cryopreserved RPE cells immediately after thawing in the suspending agent of the present invention, it shows a photoreceptor cell protection effect equal to or higher than that of transplantation after culturing the thawed cells for a certain period of time. That is, in one embodiment, cryopreserved RPE cells can be transplanted without recovery culturing after thawing. That is, the above-mentioned method for transplanting to a patient, which is characterized by the absence of a step of culturing the RPE cells after thawing, is also within the scope of the present invention.

As used herein, the "photoreceptor cell protection effect" by RPE cell refers to an effect of maintaining survival of the photoreceptor cell and protecting and normalizing retinal functions by transplantation of RPE cells.

In a clinical trial using ES cell-derived RPE cells on macular degeneration, RPE cells immediately after thawing were suspended in poloxamer-free BSS and used as they were for transplantation without involving a culturing step (the above-mentioned non-patent document 1), whereby a given treatment effect was obtained. The present invention has simultaneously provided a new problem that such conventional method has a high possibility of causing a remarkable decrease in the photoreceptor cell protection effect of RPE cell, and a means for solving the problem by adding a poloxamer (e.g., poloxamer 188) to a suspending agent. This new problem prompts reconsideration of the easy transplantation protocol performed conventionally in which, for the purpose of improving the treatment effect (photoreceptor cell protection effect) of RPE cell, RPE cells in a cryopreserved state are transported from CPC to a hospital, thawed and transplanted immediately thereafter in the hospital. The present invention has demonstrated that even when RPE cells immediately after thawing are used for transplantation, a treatment effect equivalent to that achieved by transplantation of RPE cells after culturing for a given period can be obtained by the addition of poloxamer 188, whereby it has been shown that a conventional simple transplantation protocol can be performed without impairing the treatment effect. That is, the present invention can realize a convenient and effective transplantation treatment with RPE cells.

The pharmaceutical composition of the present invention can be transplanted by subretinally injecting with a suitable transplantation device containing a syringe and a needle (e.g., MedOne0 (registered trade mark) Poly Tip (registered trade mark) Cannula 25 g/38 g etc.) into, for example, mammals (e.g., human, mouse, rat, etc., preferably human) with a retinal disease such as macular degeneration (e.g., atrophic and exudative age-related macular degeneration, Stargardt disease), Retinitis pigmentosa and the like. The pharmaceutical composition of the present invention containing a poloxamer (e.g., poloxamer 188) can improve flowability in a transplantation device and remarkably reduce the number of RPE cells remaining in the device upon injection. Therefore, the transplantation dose can be accurately determined, and evaluation judgment of a dose-dependent treatment effect can be performed accurately in clinical research, clinical trial and clinical use after approval, thus greatly contributing to the practicalization of products such as regenerative medicine and the like.

While the present invention is explained in more detail in the following by referring to Examples, the present invention is not limited in any way thereby.

EXAMPLES

Example 1. Verification of RPE Cell Protection Effect of Poloxamer 188

The protection effect of poloxamer 188, which is known to have a cell protection effect, on RPE cell was verified by measuring the cell survival rate of RPE cells over time when the RPE cells are suspended in HBSS (+) containing poloxamer 188 at various concentrations and preserved in the state of cell suspension.

Cryopreserved (STEM-CELL BANKER (registered trade mark) GMP grade) RPE cells (112007 iPS cell-derived RPE cells; iPS cell source: Kyoto University) were thawed at 37±2° C., live cell number and cell survival rate were measured by a Trypan Blue staining method, and the cells were dispensed to a cell number of $1.5 \times 10^5$ cells/tube. The RPE cells were centrifuged (200 g, 4 min, room temperature) and the supernatant was removed. HBSS (+) (450 µL) containing poloxamer 188 at a concentration of 0% (w/v), 0.005% (w/v), 0.05% (w/v), or 0.5% (w/v) was added and the resuspended RPE cell suspension was stood at 4° C., and the cell survival rate was measured over time. The poloxamer 188-containing HBSS(+) was prepared by diluting Pluronic F-68, 10% (100×) (Thermo Fisher Scientific (former Life Technologies)) with HBSS(+) (in all Examples hereafter, poloxamer 188-containing medium was prepared by a similar method). Sampling was performed at each measurement time point of immediately after suspension preparation as 0 hr, 24 hr later, 48 hr later, and cell survival rate was measured by the Trypan Blue staining method.

The results are shown in FIG. 1. FIG. 1A shows a plot of variation of cell survival rates as a measured value, and FIG. 1B shows variation of the cell survival rate after standing at 4° C. as a relative value in which the cell survival rate immediately after (0 hr later) suspension preparation is 100%. When compared to suspending in plain HBSS (+), a decrease in the cell survival rate of RPE cells suspended in 0.005% (w/v), 0.05% (w/v) poloxamer 188-containing HBSS (+) was suppressed up to 4° C. standing 48 hr (FIG. 1A). On the other hand, when compared to suspending in plain HBSS (+), the slope of decrease in the cell survival rate of RPE cells suspended in 0.5% (w/v) poloxamer 188-containing HBSS (+) is steep, and the decrease in the cell survival rate was not be suppressed (FIG. 1B). These results reveal that poloxamer 188 at addition concentrations of 0.005% (w/v) and 0.05% (w/v) suppresses a decrease in the cell survival rate. Furthermore, the addition concentration 0.5% (w/v) of poloxamer 188 could not suppress a decrease in the cell survival rate. It was suggested that cytotoxicity appears at this concentration due to the cellular membrane solubilization action of the surfactant.

Considering that the RPE cell suspension preparation operation is performed at room temperature in clinical practice, the following experiment was performed with the aim to evaluate the preservation stability of RPE cell suspension suspended in plain HBSS or 0.05% (w/v) poloxamer 188-containing BSS at room temperature and 4° C.

Cryopreserved RPE cells (112007 iPS cell-derived RPE cells; iPS cell source: Kyoto University) were thawed at 37±2° C., diluted with BSS, washed, live cell number and cell survival rate were measured by Trypan Blue staining method, and the cells were dispensed to a cell number of $3 \times 10^6$ cells/tube. The RPE cells were centrifuged (200 g, 4 min, room temperature) and the supernatant was removed. Plain HBSS or 0.05% (w/v) poloxamer 188-containing BSS (1 mL) was added and the resuspended RPE cell suspension was stood at room temperature or 4° C., and the cell survival rate was measured 6 hr later by a nucleocounter (registered trade mark) NC-200 (produced by: ChemoMetec).

Figure 2:
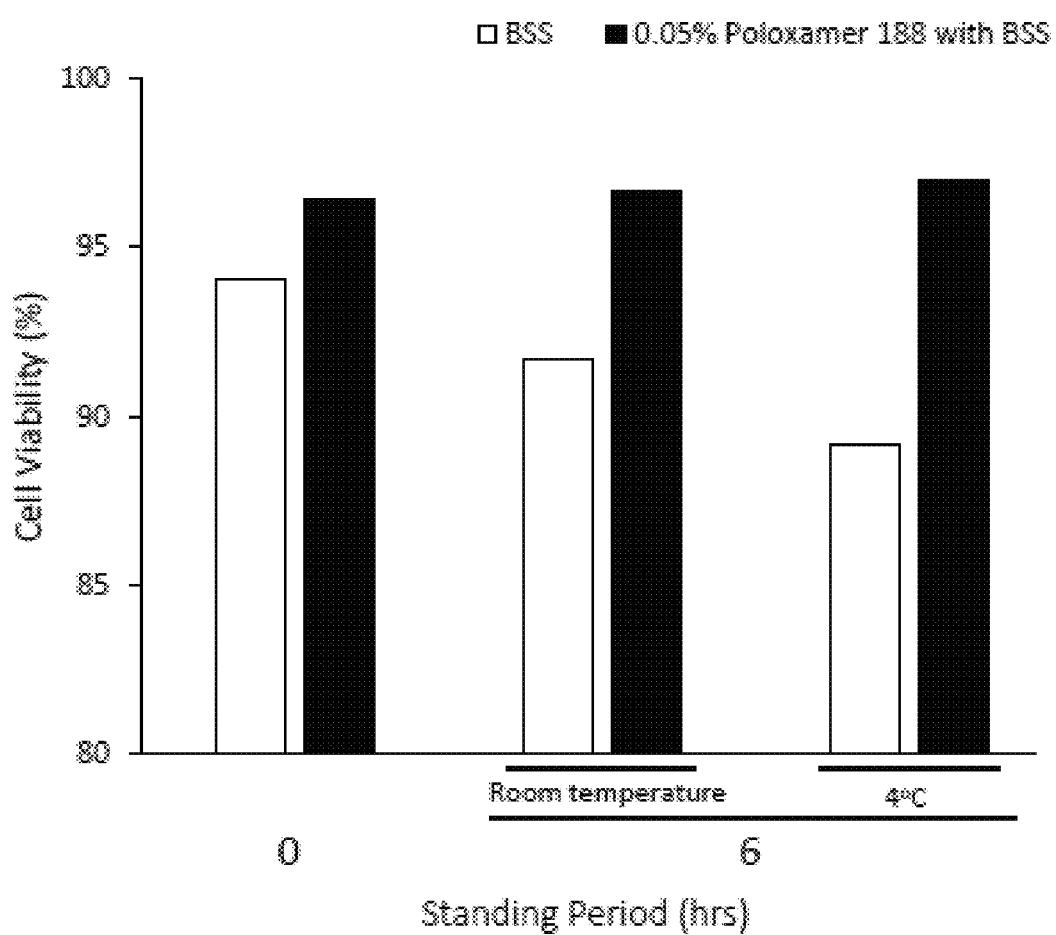
FIG. 2 shows the effect of 0.05% (w/v) poloxamer 188 on the survival rate of RPE cells stood at room temperature or 4° C. for 6 hr after freeze-thawing.

The results are shown in FIG. 2. When compared to suspending in plain HBSS, the cell survival rate of RPE cells suspended in poloxamer 188-containing BSS was maintained high at room temperature and 4° C. after standing for 6 hr. In addition, it was shown that the preservation stability of RPE cell suspension suspended in poloxamer 188-containing BSS did not change until 6 hr later when stood at room temperature and 4° C. Therefore, it was clarified that the protection effect of poloxamer 188 on RPE cell is found even at room temperature. Use of poloxamer 188-containing BSS as a medium for transplantation is also effective for preparing, storing or transporting RPE cell suspension under room temperature conditions where temperature control is easy in a special environment such as hospital CPC etc. and a remote location.

Furthermore, the following experiment was performed to verify in detail the effective concentration for the protection effect of poloxamer 188 on RPE cells.

Cryopreserved RPE cells (Ff-I01 iPS cell derived from RPE cell; iPS cell source: Kyoto University) were thawed at 37±2° C., diluted with HBSS (+) and washed. The live cell number and cell survival rate were measured using a nucleocounter (registered trade mark) NC-200 (produced by: ChemoMetec), and the cells were dispensed to $1 \times 10^6$ cells/tube, centrifuged (200 g, 4 min, room temperature), and the supernatant was removed. HBSS (+) (1 mL) containing poloxamer 188 at a concentration of 0% (w/v), 0.001% (w/v), 0.005% (w/v), 0.01% (w/v), 0.05% (w/v), or 0.1% (w/v) was added and the resuspended RPE cell suspension was stood at room temperature, and the cell survival rate was measured over time. Sampling was performed at each measurement time point of immediately after suspension preparation, 2 hr later, 4 hr later, 8 hr later, and cell survival rate was measured using a nucleocounter (registered trade mark) NC-200 (produced by: ChemoMetec).

Figure 3:
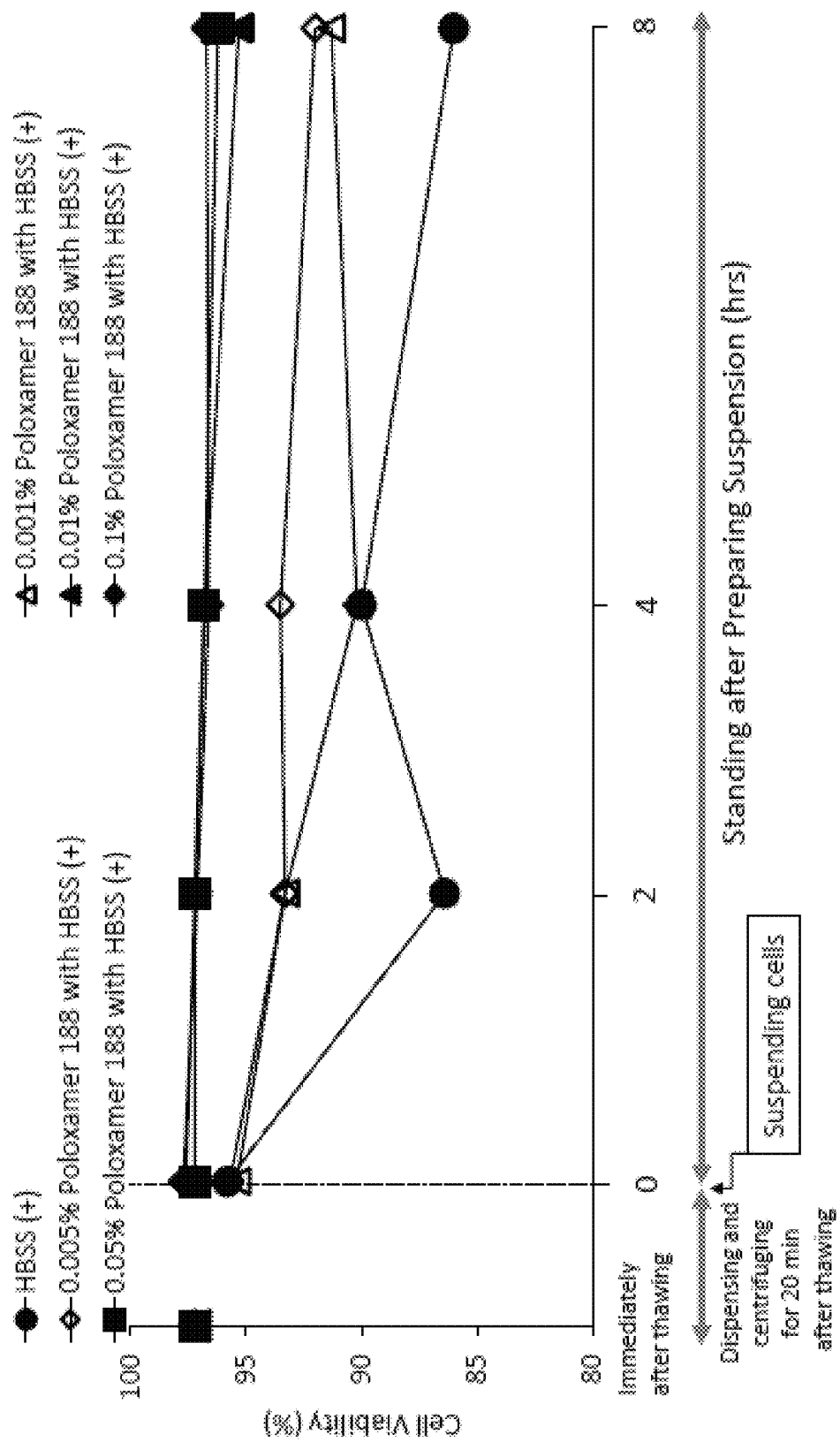
FIG. 3 shows the effect of various concentrations of poloxamer 188 on the survival rate of RPE cells stood at room temperature for 8 hr after freeze-thawing.

When compared to suspending in plain HBSS (+), the cell survival rate of RPE cells suspended in poloxamer 188-containing BSS (+) was maintained high at room temperature after standing for 8 hr at all tested poloxamer 188 concentrations (FIG. 3). A particularly high cell survival rate was shown when the concentration of poloxamer 188 was 0.01% (w/v)-0.1% (w/v). These results reveal that a concentration of poloxamer 188 preferable for RPE cell protection effect as a medium for transplantation is 0.01% (w/v)-0.1% (w/v). Consequently, under the environment during general preparation in the hospital where special conditions are not necessary, it is possible to stably maintain the cell survival rate of RPE cells for a time period presumed to be sufficient for transfer and transportation after preparation from the site of preparation, and ophthalmic surgery for transplantation, and safely perform transplantation without impairing the quality as an RPE cell preparation. In addition, use of this medium for transplantation is also effective for preparing RPE cell suspension, and storing or transporting same at ordinary temperature in a special environment such as hospital CPC etc. and a remote location.

Example 2. Photoreceptor Cell Protection Effect Test Using RCS Rat

As the effectiveness of a cell suspension using human iPS cell-derived RPE cells, the difference in the effect due to the presence or absence of a culture step after thawing and the presence or absence of addition of poloxamer 188 to a medium for transplantation was evaluated by the retina photoreceptor cell protection effect after subretinal transplantation to RCS rat as a retina denaturation rat model.

animal subject: 3-week-old RCS (Royal College of Surgeons) rat (supplied from: CLEA Japan, Inc.) was used. RCS rat is a rat having natural generation of retinal denaturation as a phenotype and widely used as a model animal of retinitis pigmentosa and age-related macular degeneration in test systems supporting effectiveness for these diseases.

test substance: RPE cells (112007 iPS cell-derived RPE cells; iPS cell source: Kyoto University) thawed immediately before transplantation and prepared as suspensions (test substances −1A and −1B) by using two different kinds of media for transplantation (BSS PLUS 500 intraocular irrigating solution 0.0184% (Nihon Alcon, hereinafter BSS), 0.05% (w/v) poloxamer 188-containing BSS) without culturing, or RPE cells thawed and cultured for 14 days after reactivating at the RPE cell production facility prior to transplantation and, without freezing, prepared as suspensions (test substances −2 and −3) by using two different kinds of media for transplantation (poloxamer 188-containing BSS, BSS) were used as a test substance.

test substance-1A: thawed RPE cells suspended in BSS
test substance-1B: thawed RPE cells suspended in poloxamer 188-containing BSS anesthetized with Benoxil ophthalmic solution 0.4% (Santen Pharmaceutical Co., Ltd.), and the eye ball surface and eyelid were disinfected with a disinfection liquid composed of 0.1% Povidone-iodine containing physiological saline. The disinfection liquid was immediately washed off from the eye ball with physiological saline. After disinfection, SCOPISOL SOLUTION FOR EYE (Senju Pharmaceutical Co., Ltd.) was instilled, and a contact lens manufactured by unicon company, disinfected with alcohol and washed with physiological saline was placed on the eye ball. Under a microscope, a hole was made in the eye ball with a needle (33 G), and a test substance or a medium was subretinally injected using Hamilton Syringe (10 μL) and needle (33 G). After completion of injection, Atipamezole Hydrochloride (ANTISEDAN; 5.0 mg/mL, Orion Pharma) was intramuscularly administered (0.72 mL/kg). A mock treatment eye ball was subjected to the same operation as for the medium and test substance administration eye balls except the injecting operation.

Pathological examination (specimen preparation): Eye ball and optic nerve were fixed with SUPER FIX (KURABO INDUSTRIES LTD.). Two days later from the date of autopsy, they were treated in a sealed apparatus for automatic fixation and embedding without washing with water. Slices were formed.

test method: Using at least one specimen for each individual (one specimen for each eye in medium group, mock treatment group, non-treatment group, 10 specimens for each eye in test substance administration group), optic papilla.optic nerve were observed. As to the number of residual photoreceptor cells, the retinal region was divided into 4 parts (transplantation side anterior part, transplantation side posterior part, non-transplantation side anterior part and non-transplantation side posterior part), the maximum number of photoreceptor cells remaining in the external granular layer for each slide in each region was scored and mean of the maximum number of each area was calculated.

TABLE 1 test group constitution

Figure 4:
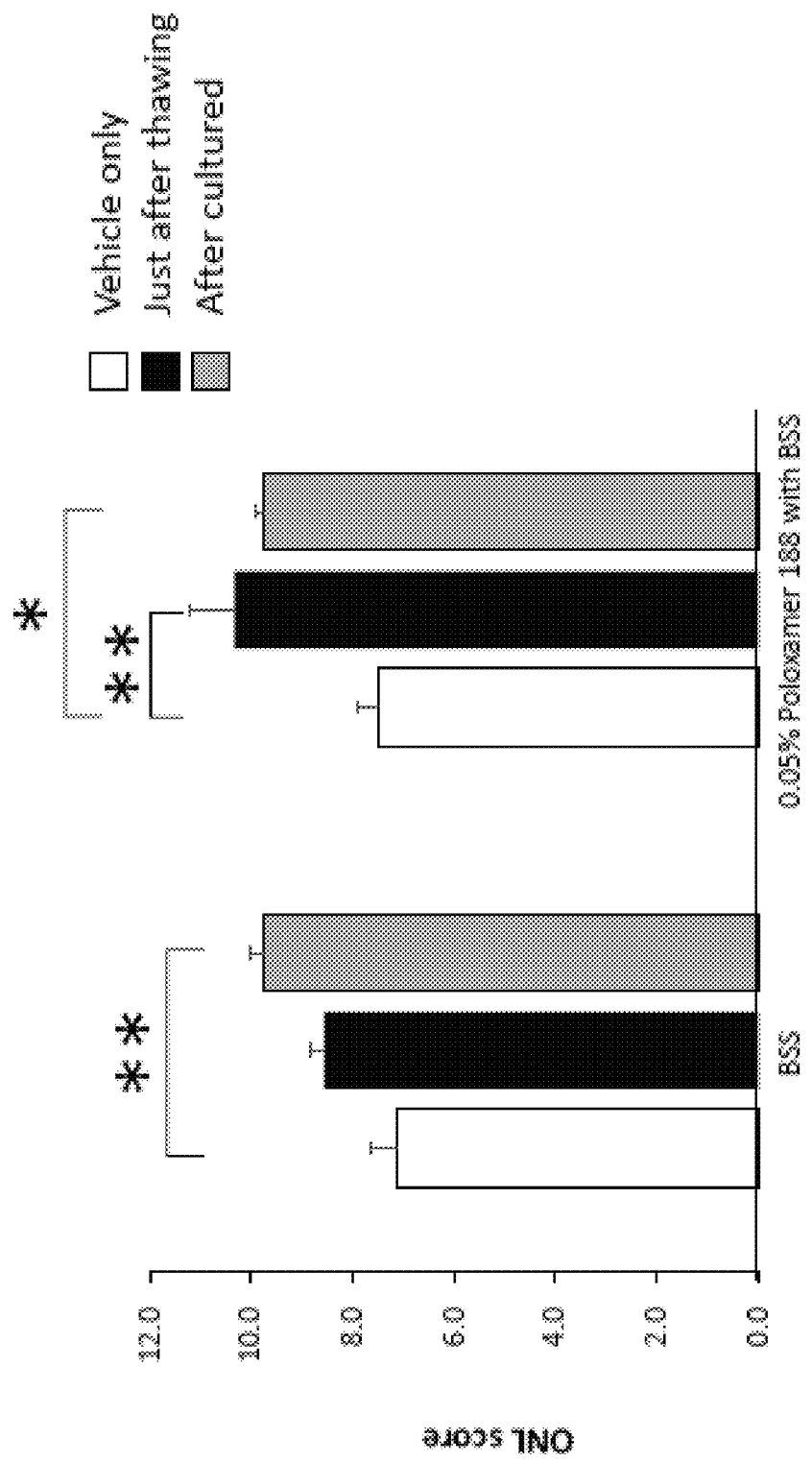
FIG. 4 shows a photoreceptor protection effect when RPE cells immediately after thawing or after culturing for 14 days after thawing were suspended in a medium (BSS) alone or a medium added with 0.05% (w/v) poloxamer 188 and transplanted to RCS rats.

| group | site of injection | test substance and control substance | amount of transplant (cells/eye) | volume (μL/eye) | concentration (cells/mL) | number of animals (animal No) male |
|---|---|---|---|---|---|---|
| 1 | right eye | test substance-1A | $1 \times 10^5$ | 2 | $5 \times 10^7$ | 7 (1-5, 8, 33) |
|   | left eye | BSS | — | — | — | |
| 2 | right eye | test substance-1B | $1 \times 10^5$ | 2 | $5 \times 10^7$ | 8 (9-16) |
|   | left eye | poloxamer 188-containing BSS | — | — | — | |
| 3 | right eye | test substance-2 | $1 \times 10^5$ | 2 | $5 \times 10^7$ | 8 (17-24) |
|   | left eye | mock treatment | — | — | — | |
| 4 | right eye | test substance-3 | $1 \times 10^5$ | 2 | $5 \times 10^7$ | 8 (25-32) |
|   | left eye | non-treatment | — | — | — | | test substance-2: cultured RPE cells suspended in poloxamer 188-containing BSS
test substance-3: cultured RPE cells suspended in BSS
transplantation method: a 9:2 (volume ratio) mixture of ketamine hydrochloride (25 mg/mL; Supriya Lifescience Ltd.) and xylazine (10 mg/mL; Bayer Yakuhin, Ltd.) was intramuscularly administered at 2.0 mL/kg for anesthesia, a mydriatic agent (MydrinP ophthalmic solution, Santen Pharmaceutical Co., Ltd.) was instilled for mydriasis. After confirmation of mydriasis, the surface of the eye ball was The results are shown in FIG. 4. When BSS was used as a medium for transplantation, the number of remaining photoreceptor cell layers (ONL score) was significantly high in the cultured RPE cell suspension (test substance-3) administration group as compared to the BSS administration group. However, when compared to the BSS administration group, the thawed RPE cell suspension (test substance-1A) administration group tended to show high values but a significant difference was not found. The results reveal that the transplanted RPE cells have a photoreceptor cell protection effect but the effect is higher in the cultured RPE cells than in the thawed RPE cells. On the other hand, when poloxamer 188-containing BSS was used as a medium for transplantation, the number of remaining photoreceptor cell layers (ONL score) was significantly and remarkably higher in the thawed RPE cell suspension (test substance-1B) and cultured RPE cell suspension (test substance-2) administration groups compared to the poloxamer 188-containing BSS administration group. More surprisingly, the thawed RPE cell suspension (test substance-1B) administration group tended to show higher values than the cultured RPE cell suspension (test substance-2) administration group.

The results reveal that use of poloxamer 188-containing BSS as a medium for transplantation results in equivalent or rather reversed photoreceptor cell protection effect of the thawed RPE cells and the cultured RPE cells. Using poloxamer 188-containing BSS as a medium for transplantation, it is possible to omit a step of culturing freeze-thawed cells for 14 days, subsequent series of steps of detaching and recovering cultured cells, preparing the cells as a cell suspension and transporting the suspension, and all tests for ensuring stable quality and performance during this period, when in use for every transplantation. Considering environmental and technical variables such as clinical setting and in-hospital preparation and the like, it was difficult to thaw frozen cells and culture the cells for a certain period in the hospital. However, using the present method, it has become possible to provide cells that retain or exhibit photoreceptor cell protection function equivalent to or higher than that of cultured cells even when a cell pharmaceutical product formulated by freezing in a production center (CPC) is thawed and immediately used in a medical front.

Example 3. Influence of Poloxamer 188 Addition on Cell Recovery Rate Upon Thawing Influence of plain HBSS (+) or 0.05% (w/v) poloxamer 188-containing HBSS (+) as a medium for transplantation to be used for thawing cryopreserved cells on the cell recovery rate after thawing was verified.

RPE cells (QHJI01 iPS cell-derived RPE cell; iPS cell source: Kyoto University) cryopreserved after preparation were thawed at 37±2° C. and suspended in plain HBSS (+) or 0.05% (w/v) poloxamer 188-containing HBSS (+). Then, the suspension was centrifuged (200 g, 4 min, room temperature) and the supernatant was removed. The cells were resuspended in the same plain HBSS (+) or poloxamer 188-containing HBSS (+), and the live cell number and the dead cell number were measured using a nucleocounter (registered trade mark) NC-200 (produced by: ChemoMetec) or a Trypan Blue staining method. The live cells in the cells cryopreserved at $2\times10^7$ cells/vial, the recovery rate of dead cells when $2\times10^7$ cells was 100% and the ratio of lost cells were calculated.

Figure 5:
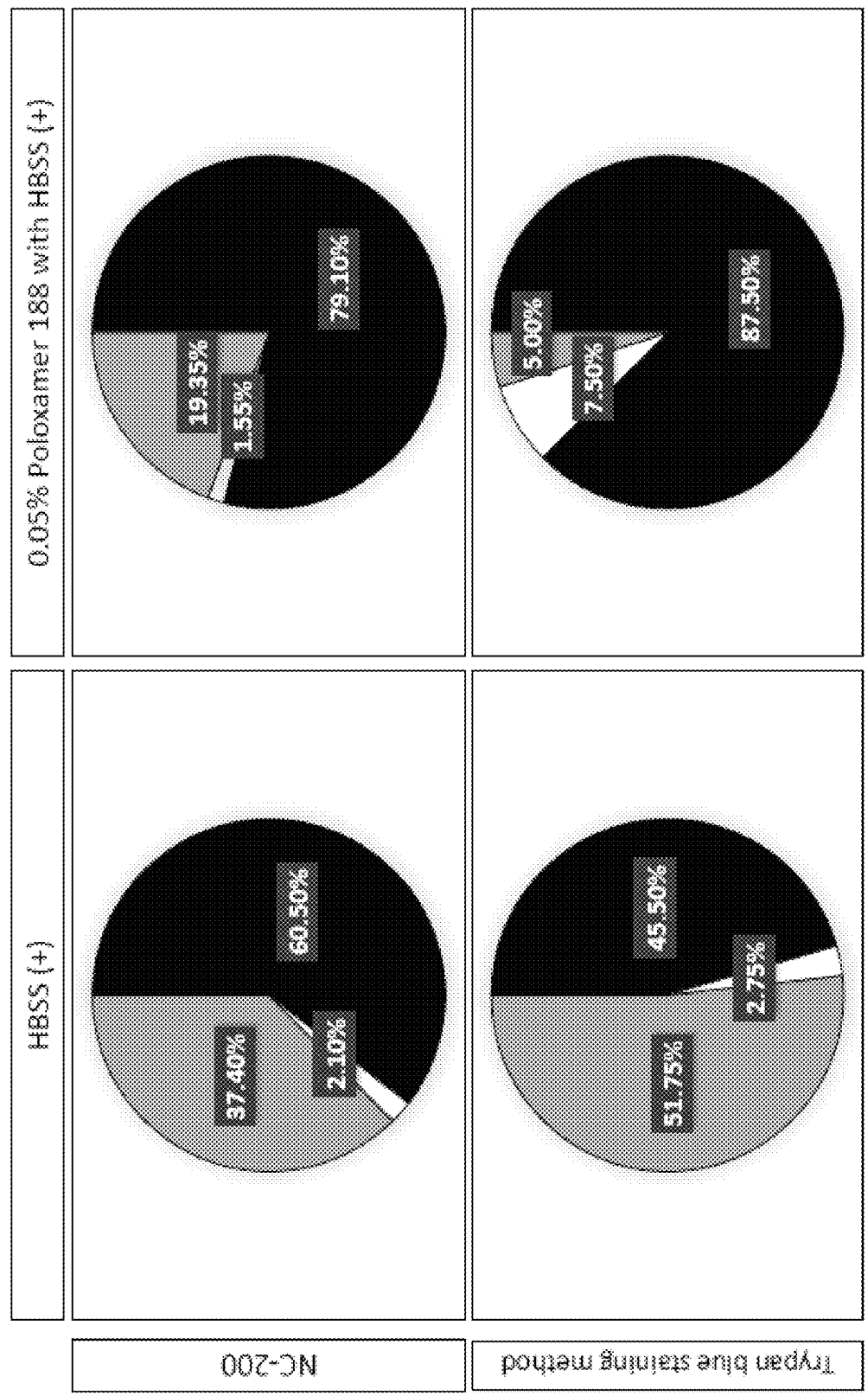
FIG. 5 shows the effect of poloxamer 188 on the recovery rate of RPE cells during thawing.

The results are shown in FIG. 5. When live cell number and dead cell number were measured using a nucleocounter (registered trade mark) NC-200 (produced by: ChemoMetec), the post-thawing recovery rate of those resuspended in plain HBSS (+) was 60.50% for live cells, 2.10% for dead cells, with the lost cells of 37.40%. On the other hand, the post-thawing recovery rate of those resuspended in 0.05% (w/v) poloxamer 188-containing HESS (+) was 79.10% for live cells, 1.55% for dead cells, with the lost cells of 19.35%. When live cell number and dead cell number were measured by a Trypan Blue staining method, the post-thawing recovery rate of those resuspended in plain HBSS (+) was 45.5% for live cells, 2.75% for dead cells, with the lost cells of 51.75%. On the other hand, the recovery rate of those resuspended in 0.05% (w/v) poloxamer 188-containing HBSS (+) was 87.50% for live cells, 7.50% for dead cells, with the lost cells of 5.00%.

From these results, it was demonstrated that the recovery rate of live cells decreased and the ratio of lost cells increased since the cryopreserved RPE cells received great damage when thawed. However, it was found that the ratio of lost cells can be greatly decreased by suspending RPE cells in 0.05% (w/v) poloxamer 188-containing HBSS (+) immediately after thawing. Reduction of cell loss by the use of 0.05% (w/v) poloxamer 188-containing HBSS (+) leads to an industrial merit of possible strict control of the number of cells in a cryopreserved preparation, as well as securing the necessary number of cells per patient and reduction of the burden cost.

Example 4. Influence of Poloxamer 188 Addition on Cell Recovery Rate in Preparation Step of Cell Suspension to be Transplanted As a transplantation medium, a cell suspension in which RPE cells are suspended in plain HESS (+) or 0.05% (w/v) poloxamer 188-containing HBSS (+) was prepared. The cell suspension was centrifuged, the supernatant was removed, the number of live cells and the number of dead cells were counted, and the recovery rate of RPE cells was calculated, based on which the influence of poloxamer 188 addition on the cell recovery rate was verified.

After thawing, RPE cells (QHJI01 iPS cell derived from RPE cells; iPS cell source: Kyoto University) washed once with a transplantation medium were suspended in the same plain HBSS (+) or 0.05% (w/v) poloxamer 188-containing HBSS (+) as in the previous step. The number of live cells was counted using a nucleocounter (registered trade mark) NC-200 (produced by: ChemoMetec) or a Trypan Blue staining method, and the RPE cell suspension was dispensed to a cell number of $1\times10^6$ cells/tube. Then, as the cell number before centrifugation, the number of live cells and the number of dead cells were counted using a nucleocounter (registered trade mark) NC-200 (produced by: ChemoMetec) or a Trypan Blue staining method. After centrifugation (200 g, 4 min, room temperature), the supernatant was removed. The RPE cells were resuspended in plain HESS (+) or poloxamer 188-containing HBSS (+). Then, as a cell number after centrifugation, the live cell number and the dead cell number were measured using a nucleocounter (registered trade mark) NC-200 (produced by: ChemoMetec) or a Trypan Blue staining method. With the number of live cells before centrifugation as 100%, the recovery rate of the cells after centrifugation was calculated.

Figure 6:
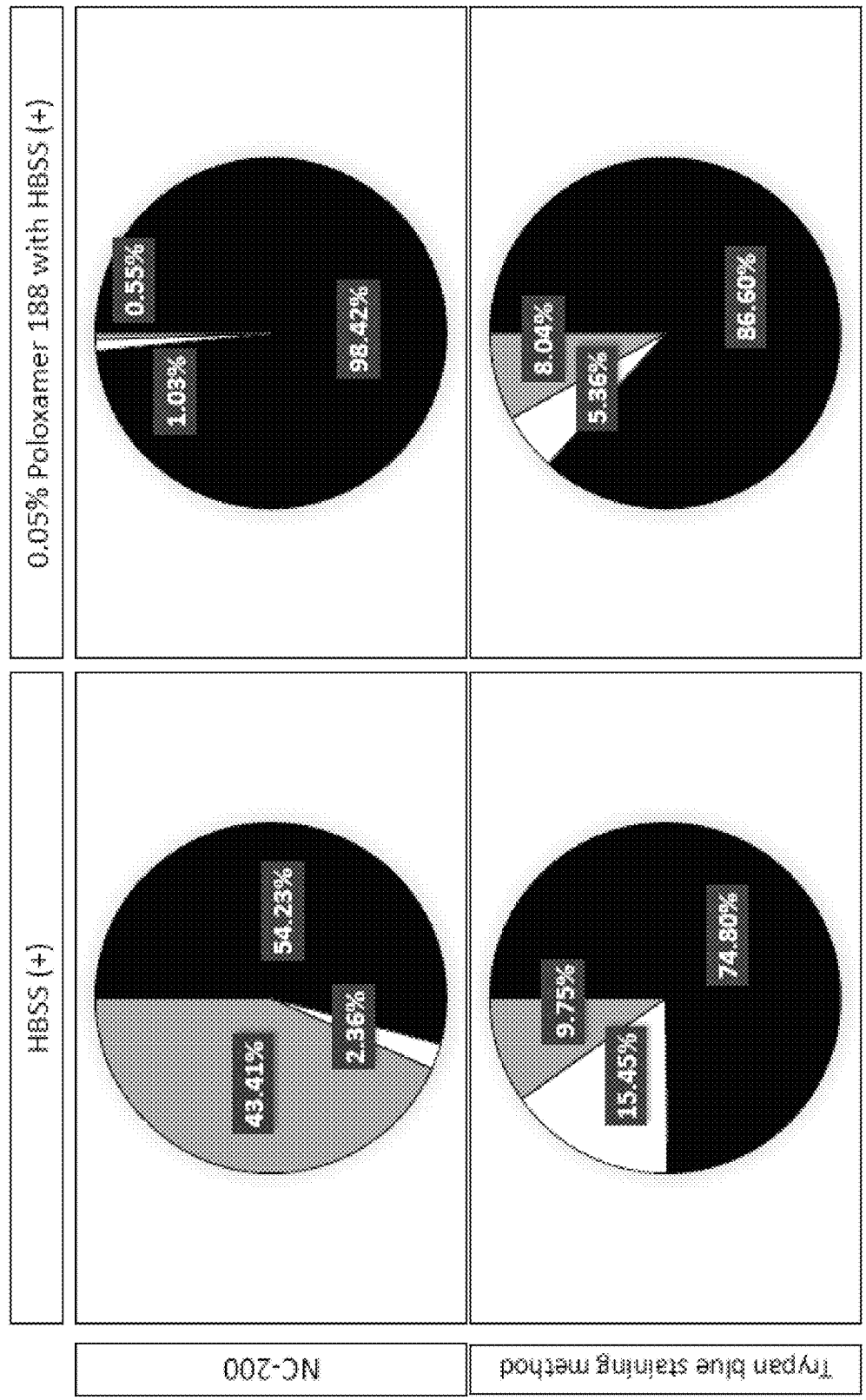
FIG. 6 shows the effect of poloxamer 188 on the recovery rate of RPE cells in a preparation step of a cell suspension to be transplanted.

The results are shown in FIG. 6. When live cell number and dead cell number were measured using a nucleocounter (registered trade mark) NC-200 (produced by: ChemoMetec), the recovery rate of those resuspended in plain HBSS (+) was 54.23% for live cells, 2.36% for dead cells, with the lost cells of 43.41%. On the other hand, the recovery rate of those resuspended in 0.05% (w/v) poloxamer 188-containing HBSS (+) was 98.42% for live cells, 1.03% for dead cells, with the lost cells of 0.55%. When live cell number and dead cell number were measured by a Trypan Blue staining method, the recovery rate of those resuspended in plain HBSS (+) was 74.80% for live cells, 15.45% for dead cells, with the lost cells of 9.75%. On the other hand, the recovery rate of those resuspended in 0.05% (w/v) poloxamer 188-containing HBSS (+) was 86.60% for live cells, 5.36% for dead cells, with the lost cells of 8.04%.

These results have demonstrated that the addition of poloxamer 188 to a transplantation medium greatly decreases the number of dead cells or the ratio of lost cells due to the centrifugation operation in the cell suspension preparation step, and improves the recovery rate of the live cells. Consequently, it is possible to reduce influences of work environment of the cell suspension preparation, for example, use instrument, and cell injury due to variations in the manipulation, etc., which are dependent on workers, of thawing and washing cells, and counting cells in the suspension, not only ensure the number of effective cells but accurately grasp the number, which in turn enables stabilization of the preparation operation of the cell suspension to be transplanted in the clinical site.

Example 5. Improvement of Passage Efficiency of RPE Cells Through Transplantation Device (MedOne (Registered Trade Mark) Poly Tip (Registered Trade Mark) Cannula 25 g/38 g)

As a transplantation medium, a cell suspension in which RPE cells are suspended in plain BSS or 0.05% (w/v) poloxamer 188-containing BSS was prepared. The passage efficiency of the cell suspension through a transplantation device was evaluated by measuring the number of live cells after passing through the transplantation device.

RPE cell (Ff-I01 iPS cell-derived RPE cells; iPS cell source: Kyoto University) suspension obtained by suspending in plain HBSS or 0.05% (w/v) poloxamer 188-containing BSS was prepared. As cells before passing through a transplantation device, the number of live cells was measured using a nucleocounter (registered trade mark) NC-200 (produced by: ChemoMetec). The cell suspensions after passing through a transplantation device were collected, and the number of live cells was measured using a nucleocounter (registered trade mark) NC-200 (produced by: ChemoMetec). With the number of live cells before passing through a transplantation device as the initial value (100%), the ratio of the number of live cells after passing through the transplantation device was calculated and the efficiency of passage through the transplantation device was evaluated.

The results are shown in Table 2. The number of live cells resuspended in plain HBSS was $1.26 \times 10^6$ cells/mL/tube (initial value) before passing through the transplantation device and $1.08 \times 10^6$ cells/mL/tube (passage efficiency 85.7%) after passing through the transplantation device. On the other hand, the number of live cells resuspended in 0.05% (w/v) poloxamer 188-containing BSS was $1.48 \times 10^6$ cells/mL/tube (initial value) before passing through the transplantation device and $1.45 \times 10^6$ cells/mL/tube (passage efficiency 98.0%) after passing through the transplantation device.

TABLE 2

|  | before passage (cells/mL/tube) | after passage (cells/mL/tube) | passage efficiency |
|---|---|---|---|
| BSS | $1.26 \times 10^6$ | $1.08 \times 10^6$ | 85.7% |
| 0.05% (w/v) Poloxamer 188 with BSS | $1.48 \times 10^6$ | $1.45 \times 10^6$ | 98.0% |

These results have demonstrated that the use of 0.05% (w/v) poloxamer 188-containing BSS as a transplantation medium improves flowability of RPE cell suspension in the transplantation device, decreases the number of cells trapped in the transplantation device, and improves passage efficiency through the transplantation device. Heretofore, there was a deviation of about 15% between the number of cells to be transplanted and the number of cells after passing through the transplantation device. However, it was clarified that the addition of poloxamer 188 greatly decreases the deviation. Consequently, the concern over a decrease in the cell survival rate of transplanted cells due to the passage through a transplantation device has been alleviated. In addition, accurate determination of the transplantation dose becomes possible, evaluation judgment of a dose-dependent treatment effect can be performed accurately in clinical study and clinical trial, and clinical use after approval, and great contribution can be made to the practicalization of products such as regenerative medicine and the like.

INDUSTRIAL APPLICABILITY

The suspending agent of the present invention containing a poloxamer (e.g., poloxamer 188) affords an improvement effect on the post-thawing survival rate of cryopreserved RPE cells, an improvement effect on the photoreceptor cell protection effect when RPE cells are transplanted immediately after thawing, and a preventive effect on cell loss in various steps from thawing to transplantation. Therefore, the pharmaceutical composition of the present invention containing RPE cells suspended in the suspending agent of the present invention is convenient for handling, also superior in a treatment effect, and extremely useful in a transplantation therapy of retinal diseases including macular degeneration.

This application is based on a patent application No. 2016-131171 (filing date: Jun. 30, 2016), the contents of which are incorporated in full herein.

The invention claimed is:

1. A pharmaceutical composition for transplantation, comprising a thawed retinal pigment epithelial (RPE) cell and a poloxamer 188,
    wherein the thawed RPE cell is suspended in a poloxamer 188-containing medium pharmaceutically acceptable as an ocular irrigating/washing solution,
    wherein the medium is a modified Hank's Balanced Salt Solution or an oxyglutathione-containing ocular irrigating/washing solution and
    wherein a concentration of the poloxamer 188 in the medium is 0.001% (w/v) -0.1% (w/v).

2. The pharmaceutical composition according to claim 1, wherein a concentration of the poloxamer 188 in the medium is 0.01% (w/v)-0.1% (w/v).

3. The pharmaceutical composition according to claim 1, wherein the thawed RPE cell is a cell within 1 hr after thawing from cryopreservation, and wherein the pharmaceutical composition is transplanted to a subject within 8 hr after preparation.

4. The pharmaceutical composition according to claim 1, showing an improved survival rate of the thawed RPE cell compared to that without containing a poloxamer 188.

5. The pharmaceutical composition according to claim 1, showing an improved recovery rate of the thawed RPE cell compared to that without containing a poloxamer 188.

6. The pharmaceutical composition according to claim 1, for protection of a photoreceptor cell.

7. A method for producing a retinal pigment epithelial (RPE) cell-containing composition, comprising suspending a thawed RPE cell in a poloxamer 188-containing medium pharmaceutically acceptable as an ocular irrigating/washing solution, wherein the medium is a modified Hank's Balanced Salt Solution or an oxyglutathione-containing ocular irrigating/washing solution and wherein a concentration of the poloxamer 188 in the medium is 0.001% (w/v)-0.1% (w/v).

8. The method according to claim 7, wherein a concentration of the poloxamer 188 in the medium is 0.01% (w/v)-0.1% (w/v).

9. The method according to claim 7, wherein the thawed RPE cell is a cell within 1 hr after thawing from cryopreservation, and wherein the RPE cell-containing composition is a pharmaceutical composition for transplantation to be transplanted to a subject within 8 hr after preparation.

10. The method according to claim 7, wherein the RPE cell-containing composition shows an improved survival rate of the RPE cell compared to that without containing a poloxamer 188.

11. The method according to claim 7, wherein the RPE cell-containing composition shows an improved recovery rate of the RPE cell compared to that without containing a poloxamer 188.

* * * * *

UNITED STATES PATENT AND TRADEMARK OFFICE
CERTIFICATE OF CORRECTION

| | |
|---|---|
| PATENT NO. | : 11,524,035 B2 |
| APPLICATION NO. | : 16/313694 |
| DATED | : December 13, 2022 |
| INVENTOR(S) | : Dai Otagiri et al. |

It is certified that error appears in the above-identified patent and that said Letters Patent is hereby corrected as shown below:

In the Claims

In Claim 2, at Column 20, Line 47, "188in" should read "188 in".

Signed and Sealed this
Twenty-eighth Day of February, 2023

Katherine Kelly Vidal
*Director of the United States Patent and Trademark Office*